United States Patent
James

(10) Patent No.: US 10,555,525 B2
(45) Date of Patent: Feb. 11, 2020

(54) METHOD OF IMPROVING TURFGRASS ABIOTIC STRESS TOLERANCE

(71) Applicant: Syngenta Participations AG, Basel (CH)

(72) Inventor: John Robert James, Greensboro, NC (US)

(73) Assignee: Syngenta Participations AG, Basel (CH)

(*) Notice: Subject to any disclaimer, the term of this patent is extended or adjusted under 35 U.S.C. 154(b) by 0 days.

(21) Appl. No.: 15/680,443

(22) Filed: Aug. 18, 2017

(65) Prior Publication Data

US 2017/0339958 A1 Nov. 30, 2017

Related U.S. Application Data

(62) Division of application No. 13/861,948, filed on Apr. 12, 2013, now Pat. No. 9,770,028.

(60) Provisional application No. 61/623,560, filed on Apr. 13, 2012.

(51) Int. Cl.
  *A01N 43/82* (2006.01)
  *A01N 37/34* (2006.01)

(52) U.S. Cl.
  CPC .............. *A01N 43/82* (2013.01); *A01N 37/34* (2013.01)

(58) Field of Classification Search
  None
  See application file for complete search history.

(56) References Cited

U.S. PATENT DOCUMENTS

| 5,523,311 | A | 6/1996 | Schurter et al. | |
| 9,770,028 | B1* | 9/2017 | James | A01N 43/82 |
| 2002/0077365 | A1* | 6/2002 | Windsor | A01N 37/10 |
| | | | | 514/621 |
| 2009/0120339 | A1* | 5/2009 | Detweiler | A01N 25/08 |
| | | | | 111/118 |

FOREIGN PATENT DOCUMENTS

| WO | 2009/095098 A2 | 8/2009 |
| WO | 2011/153442 A1 | 12/2011 |

OTHER PUBLICATIONS

Zhang et al.(Evaluation of Plant Defense Activators for Dollar Spot and Brown Patch Control on Creeping Bentgrass Putting Greens , International Turfgrass Society Research Journal, vol. 10, 2005, 180-5).*
Zhang et al.(Evaluation of Plant Defense Activators for Dollar Spot and Brown Patch Control on Creeping Bentgrass Putting Greens , International Turfgrass Society Research Journal, vol. 10, 2005, 180-5) (Year: 2005).*
Burpee et al. (Control of dollar spot of creeping bentgrass caused by an isolate of Sclerotinia homoeocarpa resistant to benzimidazole and demethylation-inhibitor fungicides, Plant disease (1997), vol. 81, No. 11, pp. 1259-1263) (Year: 1997).*
Zhang et al., International Turfgrass Society Research Journal, vol. 10, 2005, 180-185.
Lee et al., "Dollar Spot in Four Bentgrass Cultivars as Affected by Acibenzolar-S-Methyl and Organic Fertilizers", Plant Management Network, Jun. 26, 2003, pp. 1-5.

* cited by examiner

*Primary Examiner* — Alton N Pryor
(74) *Attorney, Agent, or Firm* — James Cueva

(57) ABSTRACT

The present invention relates to a method of controlling abiotic stress on turfgrass using an effective non-phytotoxic amount of acibenzolar-s-methyl.

9 Claims, No Drawings

METHOD OF IMPROVING TURFGRASS ABIOTIC STRESS TOLERANCE

This application is a divisional application of U.S. Ser. No. 13/861,948 filed Apr. 12, 2013, which claims benefit of provisional 61/623,560 filed Apr. 13, 2012, the contents of which are incorporated herein by reference.

The present invention relates to a method of improving the abiotic stress tolerance of turfgrass. More specifically, the present invention relates to a method of improving the abiotic stress tolerance of turfgrass with acibenzolar-s-methyl.

There are numerous problems that turfgrass managers face in maintaining turfgrass at a standard of quality expected by users. While the problems are many, those relating to abiotic stress (including drought stress) are particularly challenging to manage and control. For example, abiotic stress can affect turfgrass plants on golf courses causing a loss of revenue from reduced playability. One example of a common problem for golf course managers is abiotic stress caused by drought or heat.

The compound acibenzolar-S-methyl (S-methyl benzo[1,2,3]thiadiazole-7-carbothioate) acts as a functional analogue of the natural signal molecule for systemic activated resistance (SAR), salicylic acid. It activates the host plant's natural defence mechanism. The structure of acibenzolar-S-methyl can be represented as follows:

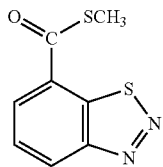 [SMILES: CSC(=O)c1cccc2nnsc12]

Acibenzolar-S-methyl is commercially available under the trade name Actigard® (Syngenta Crop Protection, Inc.).

High quality, healthy turf is essential, for example, to the golfing industry. Accordingly, there is a continued need for alternative methods to control abiotic stress on turfgrass without undue phytotoxic effects and with improved turf quality. It would be particularly useful if such methods and compositions utilized acibenzolar-S-methyl at reduced application rates.

In accordance with the present invention, it has now been discovered that the suppression or controlling of abiotic stress on turfgrass is accomplished with a non-phytotoxic turf quality improving amount acibenzolar-S-methyl. The level of turfgrass quality also is greatly enhanced by such application.

Accordingly, the present invention provides a method of suppressing or controlling abiotic stress on turfgrass which comprises applying to the turfgrass, the locus thereof or the seeds thereof, a turf quality enhancing non-phytotoxic amount of acibenzolar-s-methyl (ASM) applied at a rate of from 4 to 20 g/ha.

In accordance with the present invention, the method can be practiced with a single application that, optionally, is repeated in suitable intervals as necessary to suppress or control abiotic stress in turfgrass. Advantageously, in the practice of the method of the invention, the re-treatments or re-applications of acibenzolar-S-methyl (ASM) allow individual applications at reduced rates of from 4 to 20 g/ha per application, which enhances suppression or control abiotic stress in turfgrass over the turf growing season.

In addition, the amount of acibenzolar-S-methyl suitable for suppression or controlling abiotic stress not only is nonphytotoxic to the turfgrass, it also further improves the quality of the turfgrass to which it is applied. Accordingly, the method of the invention is useful both to (1) manage abiotic stress by suppressing or controlling the abiotic stress and (2) enhance the quality of the turfgrass to which it is applied. The method of the invention enhances the ability of end-users such as lawn care operators, golf course technicians and the like to manage, suppress or control turfgrass abiotic stress issues without undue phytotoxicity.

The methods of the present invention are applicable to any type of abiotic stress that turfgrass may experience during its growth. In a specific embodiment, the methods of the present invention are applicable when the abiotic stress experienced by a plant during its growth is drought, flood, excessive temperature, low temperature, frost, excess sunlight, insufficient sunlight, wind, inadequate soil nutrients, excessive soil salinity, air pollution, soil pollution or water pollution, or any combination thereof. Most suitably, the stress experienced is drought, excessive temperature or salinity, or any combination thereof.

In another embodiment, the method of suppressing or controlling abiotic stress, or the method to improve the quality of turfgrass comprises a treatment regime, where ASM is applied at at reduced rates of from 4 to 20 g/ha and is re-applied to the turfgrass or to the locus thereof at intervals of from 5 to 25 days, up to the cumulative maximum labeled rate for ASM per turf growing season for the specific turfgrass locus being treated according to existing restrictions.

In a more specific embodiment, in the practice of the methods of the invention, ASM is re-applied to the turfgrass or the locus thereof at intervals of from 7 to 21 days; more specifically, from 7 to 14 days, up to the cumulative maximum labeled rate for ASM for the turfgrass locus being treated.

Specific turfgrass loci suitable for the methods of the invention include those listed on the current product label for Daconil Action™ which is incorporated by reference herein. For example, suitable turfgrasses include sod farms; turf on golf courses such as roughs, fairways, tees and greens; professional and collegiate athletic fields; and lawns around commercial and industrial buildings.

In another aspect of the methods of the invention, ASM can be applied to the turfgrass or the locus thereof using turfgrass seed as a carrier.

In a further aspect, the method of suppressing or controlling abiotic stress comprises applying to the turfgrass, the locus thereof or seeds thereof a non-phytotoxic turf quality improving amount of a composition comprising acibenzolar-s-methyl.

In a further aspect, the method to improve the quality of turfgrass, or to suppress or control abiotic stress in turfgrass comprises applying to the turfgrass, the locus thereof or seeds thereof a turf quality enhancing non-phytotoxic amount of a composition comprising a mixture of a fungicide such as chlorothalonil and acibenzolar-s-methyl.

In one embodiment, in the practice of the methods of the invention, in a mixture of a fungicide such as chlorothalonil with acibenzolar-s-methyl, chlorothalonil is applied at a rate of from 2,000 to 10,000 g/ha and acibenzolar-S-methyl is applied at a rate of from 4 to 20 g/ha.

Compositions comprising ASM used in the methods of the present invention can be tank mixtures or premixes wherein the composition may further comprise adjuvants, solvents, carriers, surfactants or extenders.

A non-phytotoxic turf quality improving amount of ASM typically is a rate of from 4 to 20 g/ha per application. Typically, the application of ASM according to the method of the present invention can occur on several occasions during the turfgrass growing period or season. For example, ASM may be applied once or on several occasions during the turfgrass growth period depending on the circumstances, for example, 1 to 6 or 1 to 4 occasions, and the amounts indicated above for ASM are application rates for each application.

As used herein the phrase "quality" of turfgrass is meant to include visual quality of turfgrass and functional quality of turfgrass.

"Visual quality" of turfgrass relates to the visual appearance, such as density (the number of aerial shoots per unit area), uniformity (for example uniformity of texture, e.g. width of the leaf blades, which can be fine-textured as for example in red fescue or coarse-textured as for example in tall fescue), colour or smoothness (which affects for example the playability of a golf course).

"Functional quality" of turfgrass relates to, for example, rigidity (resistance of the turfgrass leaves to compression and is related to the wear resistance of a turf), elasticity (tendency of the turfgrass leaves to spring back once a compressing force is removed), resiliency (capacity of a turf to absorb a shock without altering its surface characteristics), ball roll (average distance a ball travels upon being released to a turf surface), yield (measure of clippings removed with mowing), verdure (measure of amount of aerial shoots remaining after mowing), rooting (amount of root growth evident at any one time during the growing season) and recuperative capacity (capacity of turfgrasses to recover from damage caused by disease organism, insects, traffic and the like).

An improvement in the quality of turfgrass can relate to one of the mentioned visual or functional quality characteristics or to any combination of these quality characteristics.

According to the present invention, an "improvement" is a measurable or noticeable increase in a given turfgrass quality characteristic over the same turfgrass quality characteristic produced under the same conditions, but without the application of the subject method.

An improvement in the quality characteristics of turfgrass is, for example, a greener or more pleasant, leaf colour of the turf.

In a further embodiment, the present invention provides a method of reducing damage to turfgrass caused by one or more abiotic stress factors, comprising the application of a non-phytotoxic turf quality improving amount acibenzolar-S-methyl, wherein the stress experienced is drought, excessive temperature (heat or cold) or salinity, or any combination thereof. Most particularly, the stress experienced is drought.

In a another embodiment, the present invention provides a method for improving the quality of turfgrass comprising the application of a non-phytotoxic turf quality improving amount acibenzolar-S-methyl, wherein the abiotic stress experienced is drought, excessive temperature (heat or cold) or salinity, or any combination thereof. More specifically, the stress experienced is drought.

According to the invention, by "turfgrass" there is understood an annual or perennial Gramineae. Said gramineae preferably belongs to one or more of the genera *Agropyron, Agrostis, Axonopus, Bromus, Buchloë, Cynodon, Eremochloa, Festuca, Lolium, Paspulum, Pennisetum, Phleum, Poa, Stenotaphrum* or *Zoysia*. More preferably, said gramineae belongs to one or more of the genera *Agrostis,*

*Buchloë, Cynodon, Eremochloa, Festuca, Lolium, Paspulum, Pennisetum, Poa, Stenotaphrum* or *Zoysia*.

According to the invention by "turf" is understood as a group of turfgrass, which covers a surface area of ground and is subject to regular maintenance.

The present invention can be practiced with all turfgrasses, including cool season turfgrass and warm season turfgrass.

Examples of cool season turfgrasses are: Bluegrasses (*Poa* L.), such as Kentucky Bluegrass (*Poa pratensis* L.), Rough Bluegrass (*Poa trivialis* L.), Canada Bluegrass (*Poa compressa* L.) and Annual Bluegrass (*Poa annua* L.); Bentgrasses (*Agrostis* L.), such as Creeping Bentgrass (*Agrostis palustris* Huds.), Colonial Bentgrass (*Agrostis tenius* Sibth.), Velvet Bentgrass (*Agrostis canina* L.) and Redtop (*Agrostis alba* L.); Fescues (*Festuca* L.), such as Creeping Red Fescue (*Festuca rubra* L.), Chewings Fescue (*Festuca rubra* var. *commutata* Gaud.), Sheep Fescue (*Festuca ovina* L.), Hard Fescue (*Festuca longifolia*), Tall Fescue (*Festuca arundinacea* Schreb.), Meadow Fescue (*Festuca elatior* L.); Ryegrasses (*Lolium* L.), such as Perennial Ryegrass (*Lolium perenne* L.), Annual (Italian) Ryegrass (*Lolium multiflorum* Lam.); Wheatgrasses (*Agropyron* Gaertn.), such as Fairway Wheatgrass (*Agropyron cristatum* (L.) Gaertn.), Western Wheatgrass (*Agropyron smithii* Rydb.). Other cool season turfgrasses include Smooth Brome (*Bromus inermis* Leyss.) and Timothy (*Phleum* L.).

Examples of warm season turfgrasses are Bermudagrasses (*Cynodon* L. C. Rich), Zoysiagrasses (*Zoysia* Willd.), St. Augustinegrass (*Stenotaphrum secundatum* (Walt.) Kuntze), Centipedegrass (*Eremochloa ophiuroides* (Munro.) Hack.), Carpetgrass (*Axonopus* Beauv.), Bahiagrass (*Paspalum notatum* Flugge.), Kikuyugrass (*Pennisetum clandestinum* Hochst. ex Chiov.), Buffalograss (*Buchloe dactyloides* (Nutt.) Engelm.) and Seashore *paspalum* (*Paspalum vaginatum* swartz).

The method according to the present invention is effective to suppress or control turfgrass against incidence of abiotic stress.

The term "locus" of turfgrass as used herein is intended to embrace the place on which the turfgrass are growing, the place where the seeds of the turfgrass are sown or the place where the seeds of the turfgrass will be placed for subsequent plant growth. According to the invention, the "locus" of a turf can relate to soil or to a substrate. An example for such a locus is a golf course, on which turfgrass is managed.

According to the invention the term "soil" means natural soil, which is typically present on a land area, such as soil being present on a golf course, or means soil, that has been modified, such as soil being granulated and/or treated with agrochemicals, such as for example fertilizers. An example of granulated and/or treated soil is disclosed in U.S. Pat. No. 5,265,372.

According to the invention the term "substrate" means a medium for the growth of turfgrass and the like, suited for application to a variety of existing ground structures. Typically, such mediums are soil-free mixtures that include sufficient proportions of ingredients of elastomeric granules, suitable binding emulsion, mineral aggregate, filler and controlled release plant nutrient particles, so that when laid and cured, said mixture produces a water permeable, resilient substrate having air pockets through which a root system of turfgrass can penetrate. Turfgrass growing on said substrate can form a turf, which can be applied to non-porous surfaces, such as for example roofs of buildings, terraces and other hard surface areas, or to porous surfaces, such as for example football fields or golf courses. Examples of such substrates are described in WO 2005/002323. Elastomeric granules can be, for example, granules of rubber, granules of recycled vehicle tyre rubber or mixtures thereof.

According to the invention the term "applied" means either simultaneously or sequentially. More specifically, in the practice of the method, ASM may be applied either simultaneously or sequentially with other active compounds typically used in managing turfgrass. If administered sequentially, the components may be administered in any order in a suitable timescale, for example, with no longer than 24 hours between the time of administering the first component and the time of administering the last component. Suitably, all the components are administered within a timescale of a few hours, such as one hour. If the components are administered simultaneously, they may be administered separately or as a tank mix or as a pre-formulated mixture of all the components or as a pre-formulated mixture of some of the components tank mixed with the remaining components.

In accordance with the method of the present invention, the ASM is applied to the turfgrass by treating the turfgrass, the locus thereof or seeds thereof.

ASM containing compositions used in the method of the invention can be prepared on site by the end-user shortly before application to the turfgrass, the locus thereof or seeds thereof by mixing in aqueous solution an ASM containing composition, an optional additional active ingredient containing composition and, optionally, a suitable surfactant or adjuvant. Such compositions are typically referred to as "tank-mix" compositions.

Alternatively, the compositions used in the method of the invention may be provided to the end-user already formulated, either at the desired dilution for application ("ready to use" compositions) or requiring dilution, dispersion, or dissolution in water by the end-user ("concentrate" compositions). Such preformulated concentrates can be liquids or particulate solids. An example of a suitable preformulated concentrate is Daconil Action.

Water application volumes for applying ASM in accordance with the method range from 500 to 1000 liters per hectare.

The amount of ASM to be applied and the number of re-treatments in the practice of a method according to the invention will depend on various factors, such as the subject of the treatment, such as, plants, turfgrass locus or seeds; the type of treatment, such as, for example spraying, spreading or seed dressing; the purpose of the treatment, such as, for example suppression or control abiotic stress; the type of abiotic stress to be controlled; enhancing turf quality, the application time; environmental conditions, the number of re-treatment intervals desired or the turfgrass species.

In yet another embodiment of the invention, the methods according to the invention are carried out by applying or treating the turfgrass, the locus thereof or seeds thereof with a turf quality enhancing non-phytotoxic amount of a composition comprising ASM, either pre-abiotic stress or under low to moderate abiotic stress conditions, where the acibenzolar-S-methyl is applied at a rate of from 4 to 20 g/ha per application.

Application to Turfgrass:

The methods according to the invention can be practiced by treating the turfgrass with an effective amount of ASM according to the invention. Within said embodiment of the invention, the ASM is suitably applied to the turfgrass by spraying or spreading. Treatment of turfgrass in accordance with the methods of the invention may be performed by lawn care operators or golf course technicians using known techniques.

In one embodiment of the inventive methods, to maintain high quality, healthy turfgrass on the intended surface area of ground, such as for example, a golf course, a sports field, a park area or a home lawn, and to protect said turfgrass against abiotic stress, ASM is applied to the turfgrass once or more than once during maintenance of the turfgrass.

Suitably, the methods of the invention are practiced by application of ASM once or more than once during a growing season of the turfgrass, in particular, at intervals of from 5 to 21 days, more particularly, at intervals of from 7 to 14 days, either pre-abiotic stress or under low to moderate abiotic stress conditions. In one embodiment, the methods of the invention comprise from 6 to 8 applications of ASM at intervals of from 7 to 14 days.

When applied to the turfgrass for enhancing suppression or control of abiotic stress, acibenzolar-S-methyl is typically applied at a rate of from 4 to 20 g/ha, suitably from 5 to 16 g/ha (greens), also suitably from 5 to 12 g/ha (fairways), more suitably from 7 to 10 g/ha (fairways).

In another aspect, suppression or control of abiotic stress is achieved by re-applying a turf quality enhancing non-phytotoxic amount of the combination of (A):(B), suitably at the foregoing rates and weight ratios, at intervals of from 5 to 21 days, suitably from 7 to 14 days, during the turf growing season.

In a particular embodiment, 6 to 8 applications of a combination (A)+(B) is applied at 14 day intervals, pre-disease or under low to moderate disease pressure during the turf growing season.

Application to the Locus of the Turfgrass:

The compositions used in the method according to the invention can be applied to the turfgrass by treating the locus of the turfgrass with a composition comprising ASM according to the invention.

Application of ASM compositions used in the method of the invention to a locus covers liquid (sprayable) or granular (active ingredient (a.i.) on inert and a.i. on fertilizer) (spreadable) applications as well.

For example, in the practice of method of the invention compositions comprising ASM can be applied to the soil before or after the seeds of the turfgrass are sown or placed into the soil; or such compositions are applied according to the method of invention to a substrate for the growth of turfgrass before or after the seeds of the turfgrass are placed into the substrate; or the compositions applied according to the method of the invention can be applied to the soil before turfgrass grown on a substrate are placed on top of the soil together with the substrate.

In one embodiment, according to the method of the invention compositions comprising ASM are applied to the turfgrass as a sprayable liquid formulation. In another embodiment, such compositions are applied to the turfgrass as a granular formulation. Suitable granules include inert and fertilizer granules. The active ingredient may be dispersed throughout, impregnated into, or coated on the surface of the granules.

Application to the Seeds of the Turfgrass:

The method according to the invention also can be practiced by applying the compositions containing ASM to the seeds of the turfgrass by treating the seeds with such a composition. When the method according to the invention involves using ASM compositions for treating seed, rates of 0.001 to 50 g of the compound mixture per kg of seed, suitably from 0.01 to 10 g per kg of seed, are generally sufficient. In one embodiment, an amount of seed used as a carrier for ASM can be applied to the soil or substrate to deliver a suitable amount of the active ingredient.

The compositions used in the methods of the invention may be employed in any conventional form, for example in the form of a twin pack, a powder for dry seed treatment (DS), an emulsion for seed treatment (ES), a flowable concentrate for seed treatment (FS), a solution for seed treatment (LS), a water dispersible powder for seed treatment (WS), a capsule suspension for seed treatment (CF), a gel for seed treatment (GF), an emulsion concentrate (EC), a suspension concentrate (SC), a suspo-emulsion (SE), a capsule suspension (CS), a water dispersible granule (WG), an emulsifiable granule (EG), an emulsion, water in oil (EO), an emulsion, oil in water (EW), a micro-emulsion (ME), an oil dispersion (OD), an oil miscible flowable (OF), an oil miscible liquid (OL), a soluble concentrate (SL), an ultra-low volume suspension (SU), an ultra-low volume liquid (UL), a technical concentrate (TK), a dispersible concentrate (DC), a wettable powder (WP) or any technically feasible formulation in combination with agriculturally acceptable adjuvants.

Said compositions used according to the methods of invention may be produced in conventional manner, e.g. by mixing the ASM with at least one appropriate formulation adjuvant.

The term "formulation adjuvant" according to the invention denotes a natural or synthetic, organic or inorganic material with which the compound of formula I is combined in order to facilitate its application to turf. This adjuvant is hence generally inert, and it must be agriculturally acceptable, in particular to turf.

The formulation adjuvant can be a carrier or a surfactant. In compositions according to the invention more than one adjuvant can be present, in such embodiments more than one carrier and/or more than one surfactant can be present, a non-limiting example would be one carrier and two surfactants.

The "carrier" can be a liquid carrier (water, alcohols, ketones, petroleum fractions, aromatic or paraffinic hydrocarbons, chlorinated hydrocarbons, liquefied gases, and the like) or a solid carrier.

Suitable liquid carriers are, but are not restricted to: aromatic hydrocarbons, in particular the fractions $C_8$ to $C_{12}$, such as xylene mixtures or substituted naphthalenes, phthalic esters such as dibutyl or dioctyl phthalate, dipropylene glycol dibenzoate, aliphatic hydrocarbons such as cyclohexane or paraffins, alcohols and glycols as well as their ethers, esters and diesters, such as ethylene glycol monomethyl ether, ketones such as cyclohexanone, strongly polar solvents such as, but not restricted to, N-methyl-2-pyrrolidone, dimethyl sulfoxide or dimethylformamide, and, if appropriate, epoxidized vegetable oils or soybean oil; or water.

Suitable solid carriers are, but are not restricted to: aluminium silicate, urea, sodium sulphate, talc, calcium sulphate or potassium sulphate and seed.

According to the invention a single carrier or a mixture of two or more carriers may be present in the composition(s) used in the methods according to the invention.

"Surfactants" are non-ionic, cationic, amphoteric and/or anionic surfactants having good emulsifying, dispersing and wetting properties. According to the invention a single surfactant or a mixture of two or more surfactants may be present. The surfactants customarily employed in formulation technology are described, inter alia, in the following publications: "McCutcheon's Detergents and Emulsifiers Annual", MC Publishing Corp., Glen Rock, N.J., 1988 and M. and J. Ash, "Encyclopedia of Surfactants", Vol. I-III, Chemical Publishing Co., New York, 1980-1981.

Among the surfactants there may be mentioned, e.g., polyacrylic acid salts, lignosulphonic acid salts, phenolsulphonic or (mono- or di-alkyl)naphthalenesulphonic acid salts, laurylsulfate salts, polycondensates of ethylene oxide with lignosulphonic acid salts, polycondensates of ethylene oxide with fatty alcohols or with fatty acids or with fatty amines, substituted phenols (in particular alkylphenols or arylphenols such as mono- and di-(polyoxyalkylene alkylphenol) phosphates, polyoxyalkylene alkylphenol carboxylates or polyoxyalkylene alkylphenol sulfates), salts of sulphosuccinic acid esters, taurine derivatives (in particular alkyltaurides), polycondensates of ethylene oxide with phosphated tristyrylphenols and polycondensates of ethylene oxide with phosphoric esters of alcohols or phenols.

A seed dressing formulation is applied in a manner known per se to the seeds employing the compositions according to the invention and a diluent in suitable seed dressing formulation form, e.g. as an aqueous suspension or in a dry powder form having good adherence to the seeds. Such seed dressing formulations are known in the art. Seed dressing formulations may contain the active ingredients in encapsulated form, e.g. as controlled release capsules or microcapsules.

The compositions used in the methods according to the invention may comprise one or more formulation additives, such as, but not limited to, biocides, anti-freeze, stickers, thickeners and compounds that provide adjuvancy effects including, for example, one or more phthalocyanines or copper phthalocyanines including pigment green such as pigment green 7; phthalocyanine green g; or pigment green 42.

In general, when phthalocyanines or copper phthalocyanines are present in compositions used in the methods according to the invention, the rate of application to the turfgrass or to the locus of the turfgrass is from 0.001 to 10 kilograms of phthalocyanine per hectare (kg/ha), suitably from about 0.01 to about 2 kg/ha, more suitably from about 0.1 to about 1 kg/ha, most suitably from about 0.2 to about 0.8 kg/ha.

The compositions used in the methods according to the invention may comprise one or more additional active ingredients, such as a fungicide, insecticide, herbicide or growth regulator. An example would be a composition that comprises a fungicide. Any suitable fungicide or herbicide may be used in the composition, for example to provide control of pests, to overcome problems and delay the onset of resistance, or to provide improved efficacy though an additive or synergistic effect of the active ingredients. Turf wetting agents may also be used in conjunction with the method of the invention. Suitable examples include Revolution® or Radiance® (Aquatrols); and Qualibra™ (Syngenta).

In one embodiment, the methods of the invention for suppressing or controlling abiotic stress on turfgrass with ASM at a rate of from 4 to 20 g/ha contemplate one or more additional active ingredients being applied selected from the list comprising azoxystrobin; trinexapac-ethyl; paclobutrazole; neonicotinoids such as thiamethoxam and imidacloprid; bisamides such as cyantraniliprole and chlorantraniliprole; fluazinam; propiconazole, difenoconazole, cyproconazole; fludioxonil; mefenoxam; cyprodinil; thiophanate methyl; iprodione; triadimefon; propamocarb; fosetyl-al; flurprimidol; flutalonil; pyraclostrobin; boscalid; vinclozolin; trifloxystrobin; myclobutanil; fenarimol; SDHI fungicides such as isopyrazam and solatenol; fluoxastrobin;

phophonic acid derivatives such as phosphonic acid, monopotassium salt; abamectin; cis-jasmone; abamectin iron chelate mixtures; and lambda cyhalothrin.

In another embodiment, the methods of the invention contemplate an abiotic stress reducing effective and non-phytotoxic amount of a composition comprising a mixture of ASM as noted above with fungicides having protectant modes of fungicidal action being applied to the turfgrass or to the locus of the turfgrass. Suitable fungicides with protectant modes of action include, for example, fluazinam and mancozeb.

The practice of the methods of the invention also contemplate application of an abiotic stress reducing effective and non-phytotoxic amount of a composition comprising a mixture of ASM with fungicides having post infection modes of fungicidal action to the turfgrass or to the locus of the turfgrass. Suitable fungicides with post-infection modes of action include, for example:

Triazoles including propiconazole, difenoconazole, cyproconazole, triticonazole, metconazole, triadimefon and tebuconazole Strobilurins including azoxystrobin trifloxystrobin, fluoxastrobin and pyraclostrobin Fludioxonil Thiabendazole, SDHIs including—boscalid, fluopyram, isopyrazam, penthiopyrad, solatenol Phenylamides including metalaxyl and mefonoxam.

The practice of the methods of the invention further contemplate application of an abiotic stress reducing effective and non-phytotoxic amount of a composition comprising a mixture of plant growth regulators and acibenzolar-S-methyl to the turfgrass or to the locus of the turfgrass. Suitable plant growth regulators for use in the inventive method include azole PGR Chemistry (such as uniconazole, and paclobutrazol), cyclohexane carboxylates (such as trinexapac-ethyl, and prohexadione-calcium), pyrimidinyl carbinols (such as flurprimidol, and ancymidol), quarternary ammoniums (such as chlormequat-chloride, and mepiquat-chloride), and sulphonyl-amino phenyl-acetamides (such as mefluidide). Plant growth regulators such as trinexapac-ethyl are suitable for use with ASM in the practice of the method on turf to reduce abiotic stress while continuing to improve turf colour, quality, reduce clippings and improve rooting.

In general, the compositions according to the invention include from 0.01 to 90% by weight of a compound of ASM, from 0 to 20% surfactant and from 10 to 99.99% carrier.

Concentrated forms of compositions used in the methods according to the invention generally contain in between about 2 and 80%, preferably between about 5 and 70% by weight of ASM. Application forms of formulation may for example contain from 0.01 to 20% by weight, preferably from 0.01 to 5% by weight of ASM. Whereas commercial products will preferably be formulated as concentrates, the end user will normally employ diluted formulations.

The compound acibenzolar-s-methyl (ASM) is commercially available.

In a one embodiment of the present invention, compositions suitable for use in the methods according to the invention comprise 53.94% chlorothalonil, 0.11% acibenzolar-S-methyl and 45.95% inert ingredients, such as a composition sold under the designation Daconil Action™ (Syngenta)

The Examples which follow serve to illustrate the invention, "active ingredient" denoting a compound ASM.

FORMULATION EXAMPLE

Suspension Concentrate

| Active ingredient | 40% |
|---|---|
| Propylene glycol | 10% |
| Nonylphenol polyethylene glycol ether (15 mol of ethylene oxide) | 6% |
| Sodium lignosulfonate | 10% |
| Carboxymethylcellulose | 1% |
| Silicone oil (in the form of a 75% emulsion in water) | 1% |
| Water | 32% |

In preparing and SC, the finely ground active ingredients are mixed with the adjuvants, giving a suspension concentrate from which suspensions of any desired dilution can be obtained by dilution with water. Using such dilutions, living plants as well as plant propagation material can be treated and protected against infestation by microorganisms, by spraying, pouring or immersion.

The following examples are for illustrative purposes only. The examples are not intended as necessarily representative of the overall testing performed and are not intended to limit the invention in any way.

BIOLOGICAL EXAMPLES

Acibenzolar-S-methyl applied in combination with chlorothalonil has provided turfgrass drought tolerance compared to chlorothalonil applied alone and an untreated check.

Example 1

Greenhouse grown creeping bentgrass (*Agrostis stolonifera*) was treated with Daconil Action (a commercially available chlorothalonil-ASM formulation; Syngenta) and Daconil Weatherstik (a commercially available chlorothalonil formulation; Syngenta) at 3.6 fluid ounces per 1000 square feet of turf. Daconil Action contains 54% chlorothalonil and 0.176% acibenzolar-S-methyl. Daconil Weatherstik contains 54% chlorothalonil. Rates are equivalent to the following:

| Treatment | Rate-fluid ounces/ 1000 sq. ft. | Chlorothalonil g ai/ha | acibenzolar-S-methyl g ai/ha |
|---|---|---|---|
| Daconil Action | 3.6 | 8250 | 16.5 |
| Daconil Weatherstik | 3.6 | 8250 | |

Two applications were applied on a 7 day interval. Bentgrass plants were maintained in the greenhouse. Watering was stopped and drought stress imposed in Daconil Action and Daconil Weatherstik treatments 3 days after the last application. The untreated check continued to be watered. Turf quality was rated on a 1-9 scale with 9 being equal to the watered check, 6 being acceptable, and 1 being dead.

Quality ratings 13 days after drought stress was imposed are included in Table 1. Turfgrass treated with Daconil Action maintained an acceptable quality rating of 6.2. This was significantly (P=0.05) different from trufgrass treated with Daconil Weatherstik.

TABLE 1

Quality Rating from Turfgrass Treated with Daconil Action and Daconil Weatherstik 13 Days After Drought Stress Was Imposed in the Greenhouse.

| Treatment | Rate oz/1000 sq. ft. turf | Quality Rating* |
|---|---|---|
| Check (watered) |  | 9.0 a** |
| Daconil Weatherstik | 3.6 | 2.1 c |
| Daconil Action | 3.6 | 6.2 b |

*Rated on a 1-9 scale with 9 being equal to the watered check, 6 being acceptable, and 1 being dead.
**Means with same letter not different, LSD (P = 0.05)

These data support the claim of enhanced drought tolerance in turfgrass when acibenzolar-S-methyl is applied in combination with chlorothalonil. Daconil Action is a unique blend of a multiple-site contact fungicide (chlorothalonil) with acibenzolar-S-methyl a systemic compound used for control of disease through induction of host plant resistance. The mode of action of acibenzolar-S-methyl mimics the natural systemic activated resistance (SAR) response found in most plant species. This SAR response does not involve direct activity against the target pathogens but relies on the plants natural defense mechanism. The SAR response activated by acibenzolar-S-methyl allows the plant to defend itself against abiotic stresses such as drought, heat, cold and salinity.

Example 2

Greenhouse grown creeping bentgrass (*Agrostis stolonifera*) was treated with Daconil Action and Daconil Weatherstik at 3.6 fluid ounces per 1000 square feet of turf. Daconil Action contains 54% chlorothalonil and 0.176% acibenzolar-S-methyl. Daconil Weatherstik contains 54% chlorothalonil. Rates are equivalent to the following:

| Treatment | Rate-fluid ounces/ 1000 sq. ft. | Chlorothalonil g ai/ha | acibenzolar-S-methyl g ai/ha |
|---|---|---|---|
| Daconil Action | 3.6 | 8250 | 16.5 |
| Daconil Weatherstik | 3.6 | 8250 |  |

Two applications were applied on a 7 day interval. Bentgrass plants were maintained in the greenhouse. Watering was stopped and drought stress imposed on the check and plants treated with Daconil Action and Daconil Weatherstik 4 days after the last application. Turf quality was rated on a 1-9 scale with 9 being best, 6 being acceptable, and 1 being dead.

Quality rating taken 4-10 days after drought stress was imposed are included in Table 2. Turfgrass treated with Daconil Action maintained an acceptable quality rating for at least 2 days longer than turf treated with Daconil Weatherstik. This was significantly (P=0.05) from turfgrass treated with Daconil Weatherstik.

TABLE 2

Quality Rating from Turfgrass Treated with Daconil Action and Daconil Weatherstik 4-10 Days Days After Drought Stress Was Imposed in the Greenhouse.

| | Rate oz/ 1000 sq ft | Days After Drought Stress was Imposed | | | | | | |
|---|---|---|---|---|---|---|---|---|
| | | 4 | 5 | 6 | 7 | 8 | 9 | 10 |
| Check | | 8.75a | 8.63a | 6.13b | 5ab | 3.75b | 3b | 2.25b |
| Daconil Weatherstik | 3.6 | 8.38a | 8.25a | 6.38b | 5.38b | 4b | 3.5b | 3.13ab |
| Daconil Action | 3.6 | 9a | 9a | 7.88a | 7.25a | 6.38a | 5.75a | 5.25a |

These results support the claim of enhanced drought tolerance in turfgrass when acibenzolar-S-methyl is applied in combination with chlorothalonil.

Example 3

Greenhouse grown creeping bentgrass (*Agrostis stolonifera*) was treated with Daconil Action and Daconil Weatherstik at 2 and 3.6 fluid ounces per 1000 square feet of turf. Daconil Action contains 54% chlorothalonil and 0.176% acibenzolar-S-methyl. Daconil Weatherstik contains 54% chlorothalonil. Rates are equivalent to the following:

| Treatment | Rate-fluid ounces/ 1000 sq. ft. | Chlorothalonil g ai/ha | acibenzolar-S-methyl g ai/ha |
|---|---|---|---|
| Daconil Action | 2.0 | 4600 | 9.2 |
| Daconil Action | 3.6 | 8250 | 16.5 |
| Daconil Weatherstik | 2.0 | 4600 | |
| Daconil Weatherstik | 3.6 | 8250 | |

Three applications were applied on a 14 day interval. Bentgrass plants were maintained in the greenhouse. Watering was stopped and drought stress imposed on the check and plants treated with Daconil Action and Daconil Weatherstik immediately after the last application. Plants were re-watered 15 days after drought stress was imposed. Turf quality was rated on a 1-9 scale with 9 being best, 6 being acceptable, and 1 being dead.

Quality rating 12-15 days after watering was stopped are included in Table 3. Turfgrass treated with both rates of Daconil Action maintained a improvement in turf quality over the untreated check and plants treated with Daconil Weatherstik in ratings taken 15 days after drought stress was imposed in the greenhouse. This significant (P=0.05) improvement continued to be evident after rewatering.

TABLE 3

Quality Rating from Turfgrass Treated with Daconil Action and Daconil Weatherstik After Drought Stress Was Imposed in the Greenhouse.

| Treatment | Rate oz/ 1000 sq. ft. | Turf Quality (1-9 Scale)* Days After Drought Stress Was Imposed | | | | |
|---|---|---|---|---|---|---|
| | | 12 | 13 | 14 | 15 | 3DARW*** |
| Check | | 6.3 a** | 2.8 bc | 1.8 bc | 1.1 b | 1.2 c |
| Daconil Action | 3.6 | 7.4 a | 6.7 a | 5.6 a | 5.7 a | 6.2 a |
| Daconil Action | 2 | 7.7 a | 6.8 a | 5.6 a | 5 ab | 5.7 a |
| Daconil Weather Stik | 3.6 | 6.7 a | 4.4 abc | 3.3 abc | 2 c | 2.2 c |

TABLE 3-continued

Quality Rating from Turfgrass Treated with
Daconil Action and Daconil Weatherstik
After Drought Stress Was Imposed in the Greenhouse.

| Treatment | Rate oz/ 1000 sq. ft. | Turf Quality (1-9 Scale)* Days After Drought Stress Was Imposed | | | | |
|---|---|---|---|---|---|---|
| | | 12 | 13 | 14 | 15 | 3DARW*** |
| Daconil Weather Stik | 2 | 6.5 a | 3.7 abc | 2.1 bc | 2.1 c | 2.3 c |

*Rated on a 1-9 scale with 9 being equal to the watered check, 6 being acceptable, and 1 being dead.
**Means with same letter not different, LSD (P = 0.05)
***DARW = Days after re-watering These results support the claim of enhanced drought tolerance in turfgrass when acibenzolar-S-methyl is applied in combination with chlorothalonil.

Example 4

Greenhouse grown creeping bentgrass (*Agrostis stolonifera*) was treated with Daconil Action at 3.5 fluid ounces per 1000 sq. ft. of turf. Daconil Action contains 54% chlorothalonil and 0.176% acibenzolar-S-methyl. Daconil Action was compared to Actigard 50WP which contains 50% acibenzolar-S-methyl. Rates are equivalent to the following:

| Treatment | Chlorothalonil g ai/ha | acibenzolar-S-methyl g ai/ha |
|---|---|---|
| Daconil Action | 8250 | 16.5 |
| Actigard 50WP | | 30 |

The purpose of the trial was to compare multiple applications of Daconil Action (16.5 g ai/ha of acibenzolar-S-methyl) with a single application of Actigard (30 g ai/ha acibenzolar-S-methyl). Two applications of Daconil Action were applied on a 7 day interval prior to inducing drought stress. A single application of Actigard was applied at the same time as the second Daconil Action application. Bentgrass plants were maintained in the greenhouse. Watering was stopped and drought stress imposed on the check and plants treated with Daconil Action and Actigard immediately after the second application of Daconil Action and the single Actigard application. Turf quality was rated on a 1-9 scale with 9 being best, 6 being acceptable, and 1 being dead.

Quality rating 11-13 days after watering was stopped are included in Table 4. Turfgrass treated with Daconil Action maintained a significant (P=0.10) improvement in turf quality over the untreated check and plants treated with Actigard in ratings taken 11-13 days after drought stress was imposed.

These data support the claim that multiple applications of Daconil Action applying 16.5 g ai/ha of acibenzolar-S-methyl are more effective than a single application acibenzolar-S-methyl in reducing drought stress symptoms. These applications are non-phytotoxic to turf.

Example 5

Greenhouse grown creeping Kentucky Bluegrass (*Poa pratensis*) was treated with Daconil Action and Daconil Weatherstik at 2 and 3.5 fluid ounces per 1000 square feet of turf. Daconil Action contains 54% chlorothalonil and 0.176% acibenzolar-S-methyl. Daconil Weatherstik contains 54% chlorothalonil. Rates are equivalent to the following:

| Treatment | Rate-fluid ounces/ 1000 sq. ft. | Chlorothalonil g ai/ha | acibenzolar-S-methyl g ai/ha |
|---|---|---|---|
| Daconil Action | 2.0 | 4600 | 9.2 |
| Daconil Action | 3.5 | 8250 | 16.5 |
| Daconil Weatherstik | 2.0 | 4600 | |
| Daconil Weatherstik | 3.5 | 8250 | |

The purpose of the trial was to compare multiple applications of Daconil Action (16.5 g ai/ha of acibenzolar-S-methyl) to Daconil Weatherstik for reduction in heat stress. Four applications of Daconil Action and Daconil Weatherstik were applied on a 7 day interval prior to inducing heat stress. Kentucky Bluegrass plants were maintained in an incubator. Heat stress imposed on the check and plants treated with Daconil Action and Daconil Weatherstik immediately after the last application. Temperatures were maintained at 35 degrees C. during the day and 30 degrees C. at night. Turf quality was rated on a 1-9 scale with 9 being best, 6 being acceptable, and 1 being dead.

Quality rating 11-13 days after watering was stopped are included in Table 5. Turfgrass treated with Daconil Action maintained a significant (P=0.10) improvement in turf quality over the untreated check and plants treated with Actigard in ratings taken 11-13 days after drought stress was imposed.

TABLE 4

Quality Rating from Turfgrass Treated with Daconil Action and Actigard After Drought Stress Was Imposed in the Greenhouse.

| | Rate g ai/ha | Application Timing | Turf Quality (0-9scale)* Days After Drought Stress was Imposed | | | |
|---|---|---|---|---|---|---|
| | | | 11 (8:00 AM) | 11 (4:30 PM) | 12 | 13 |
| Check | | | 6.63a** | 4.25b | 3.62a | 2.38ab |
| Daconil Action | 8200 | 2 applications, 7 day interval | 7.25a | 6.25a | 5.75a | 3.75a |
| Actigard | 30 | Single application | 6.63a | 4.75ab | 3.18a | 2.00ab |

*Rated on a 1-9 scale with 9 being equal to the watered check, 6 being acceptable, and 1 being dead.
**Means with same letter not different, LSD (P = 0.10)

TABLE 5

Quality Rating from Turfgrass Treated with Daconil Action and
Daconil Weatherstik After Drought Stress Was Imposed in an incubator.

| | | Application Timing | Turf Quality (0-9 scale)* Days After Heat Stress was Imposed | |
|---|---|---|---|---|
| | | | 7 | 12 |
| Check | | | 3.25a** | 3.00abc |
| Daconil Action | 3.5 | 4 applications 7 day interval | 3.81a | 3.75ab |
| Daconil Action | 2.0 | 4 applications 7 day interval | 3.75a | 3.5ab |
| Dacinil Weatherstik | 3.5 | 4 applications 7 day interval | 1.75b | 2.06cd |
| Daconil Weatherstik | 2.0 | 4 applications 7 day interval | 1.68b | 1.93cd |

*Rated on a 1-9 scale with 9 being equal to the watered check, 6 being acceptable, and 1 being dead.
**Means with same letter not different, LSD (P = 0.10)

These data support the claim that multiple applications of DaconilAction applying 9.2 and 16.5 g ai/ha of acibenzolar-S-methyl are more effective than Daconil Weatherstik in reducing heat stress symptoms in turf. These applications are non-phytotoxic to turf.

Although the invention has been described with reference to preferred embodiments and examples thereof, the scope of the present invention is not limited only to those described embodiments. As will be apparent to persons skilled in the art, modifications and adaptations to the above-described invention can be made without departing from the spirit and scope of the invention, which is defined and circumscribed by the appended claims. All publications cited herein are hereby incorporated by reference in their entirety for all purposes to the same extent as if each individual publication were specifically and individually indicated to be so incorporated by reference.

The invention claimed is:

1. A method for controlling or suppressing abiotic stress in turfgrass, comprising applying to the turfgrass or to the locus of the turfgrass, a turf quality improving non-phytotoxic amount of a composition comprising a mixture of acibenzolar-S-methyl and fluazinam, wherein the acibenzolar-S-methyl is applied at a rate of from 4 to 20 g/ha.

2. The method of claim 1, wherein the composition is applied pre-abiotic stress or under low to moderate abiotic stress conditions.

3. The method of claim 1, wherein the fluazinam and acibenzolar-S-methyl are applied simultaneously together, separately, or in succession.

4. The method of claim 1, wherein the composition further comprises adjuvants, solvents, carrier, surfactants or extenders.

5. The method according to claim 4, wherein the composition comprises from 0.01 to 90% by weight of the acibenzolar-S-methyl, from 10 to 99.99% of a carrier and from 0 to 20% of a surfactant.

6. The method of claim 1, wherein acibenzolar-S-methyl is applied at the rate of from 5 to 16 g/ha.

7. The method of claim 1, further comprising applying the composition at intervals of from 5 to 21 days, either pre-abiotic stress or under low to moderate abiotic stress conditions, during the turf growing season.

8. The method of claim 7, wherein 6 to 8 applications of the composition is applied at intervals of from 7 to 14 days.

9. The method according to claim 1, wherein the turfgrass is an annual or perennial Gramineae belonging to at least one of the genera *Agropyron, Agrostis, Axonopus, Bromus, Buchloë, Cynodon, Eremochloa, Festuca, Lolium, Paspulum, Pennisetum, Phleum, Poa, Stenotaphrum* or *Zoysia*.

* * * * *